United States Patent
Yamka et al.

(10) Patent No.: US 8,524,288 B2
(45) Date of Patent: *Sep. 3, 2013

(54) COMPOSITIONS AND METHODS FOR ALTERING STOOL QUALITY IN AN ANIMAL

(75) Inventors: Ryan Michael Yamka, Topeka, KS (US); Kim Gene Friesen, Carthage, IN (US)

(73) Assignee: Hill's Pet Nutrition, Inc., Topeka, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 13/195,887

(22) Filed: Aug. 2, 2011

(65) Prior Publication Data

US 2011/0280954 A1 Nov. 17, 2011

Related U.S. Application Data

(62) Division of application No. 12/264,615, filed on Nov. 4, 2008, now Pat. No. 8,057,828, which is a division of application No. 11/774,975, filed on Jul. 9, 2007.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

| | | | |
|---|---|---|---|
| 3,898,328 | A | 8/1975 | Beigler et al. |
| 4,164,568 | A | 8/1979 | Bywater |
| 5,028,437 | A | 7/1991 | Jerrett |
| 5,616,569 | A | 4/1997 | Reinhart |
| 6,066,341 | A | 5/2000 | Wilson |
| 6,280,779 | B1 | 8/2001 | Nadeau et al. |
| 6,514,521 | B1 | 2/2003 | Julien |
| 6,517,877 | B2 | 2/2003 | Gannon |
| 2004/0253324 | A1 | 12/2004 | Hill |
| 2007/0190171 | A1 | 8/2007 | Yamka et al. |

FOREIGN PATENT DOCUMENTS

| | | |
|---|---|---|
| EP | 0226332 | 6/1987 |
| EP | 0382306 | 8/1990 |
| FR | 2252848 | 6/1975 |
| GB | 2319727 | 6/1998 |
| JP | H02-200164 A | 8/1990 |
| JP | 3-061452 A | 3/1991 |
| JP | H04-166039 A | 6/1992 |
| JP | 7-118162 A | 5/1995 |
| JP | H10-304825 A | 11/1998 |
| JP | 2001-521725 A | 11/2001 |
| JP | 2002-536002 A | 10/2002 |
| JP | 2003-522788 A | 7/2003 |
| JP | 2007-512024 A | 5/2007 |
| JP | 2009-514554 A | 4/2009 |
| RU | 2223770 C2 | 2/2004 |
| WO | WO 85/01657 | 4/1985 |
| WO | WO 96/25940 | 8/1996 |
| WO | WO 01/049130 | 7/2001 |
| WO | WO 01/82898 | 11/2001 |
| WO | WO 2007/065172 | 6/2007 |
| WO | WO 2007/082143 | 7/2007 |

OTHER PUBLICATIONS

Dersjant et al., 2001, "Feed Intake, Growth, Digestibility of Non Dry Matter and Nitrogen in Young Pigs as Affected by Dietary Cation-Anion Difference and Supplementation of Xylanase", J. of Animal Physiology and Animal Nutrition 85(3-4):101-109.
Gomide et al., 2004, Arquivo Brasileiro de Medicina Veternaria e Zootecnia, 56(3):363-369.
Hernot et al., 2004, "Relationship Between Electrolyte Apparent Absorption and Fecal Quality in Adult Dogs Differing in Size", J. Nutrition 134:2031S-2034S.
Ingredients101.com, 2009, 2 pages.
Johnson et al., 1985, "The Effects of Dietary Minerals and Electrolytes on the Growth and Physiology of the Young Chick", J. Nutrition 115:1680-1690.
Mason, "Dietary Cation-Anion Balance", Alberta Dairy Management, date created May 20, 1997, Obtained online at http://www.agromedia.ca/ADM_Articles/content/dcab.pdf.
Meyer et al., 1999, "Digestibility and Compatibility of Mixed Diets and Faecal Consistency in Different Breeds of Dog", J. Veterinary Medicine 46(3):155-165.
Stutz et al., 1992, "Effects of Dietary Cation-Anion Balance on Blood Parameters in Exercising Horses", J. of Equine Veterinary Science 12(3):164-167.
Sunvold et al., 1995, "Dietary Fiber for Dogs: IV. In vitro Fermentation of Selected Fiber Sources by Dog Fecal Inoculum and in vivo Digestion and Metabolism of Fiber-Supplemented Diets", J. Animal Science 73:1099-1109.
Takagi et al., 1991, "Nutrition, Feeding, and Calves: Effects of Manipulating Dietary Cation-Anion Balance on Macromineral Balance in Sheep", J. Dairy Science 74:4202-4214.
Yamka et al., 2006, "In vivo Measurement of Flatulence and Nutrient Digestibility in Dogs Fed Poultry By-Product Meal, Conventional Soybean Meal, and Low-Oligosaccharide Low-Phytate Soybean Meal", American J. Veterinary Research 67(1):88-94.
Ahmad et al., 2005, "Influence of Varying Sources of Dietary Electrolytes on the Performance of Broilers Reared in a High Temperature Environment," Animal Feed Science and Tech. 120(3-4):277-298.
Baker et al., 1991, "Comparitive Nutrition of Cats and Dogs," Ann. Rev. Nutrition 11:239-263.
Bieberdorf et al., 1972, "Pathogenesis of Congenital Alkalosis with Diarrhea," J. Clin. Investigation 51:1958-1968.
Burrows et al., 1982, "Effects of Fiber on Digestibility and Transit Time in Dogs," J. Nutr. 112:1726-1732.
Database WPI Week 199117, 1995, Derwent Publications Ltd. AN: 1995-203745, Abstract.

(Continued)

*Primary Examiner* — Michael Meller
(74) *Attorney, Agent, or Firm* — Thomas M. Hunter

(57) ABSTRACT

The present invention provides compositions and methods for improving stool quality of a puppy by adjusting the balance of metabolizable cations to metabolizable anions consumed by the puppy.

7 Claims, No Drawings

(56) References Cited

OTHER PUBLICATIONS

Dersjant-Li et al., 2001, "Performance, digesta characteristics, nutrient flux, plasma composition, and organ weight in pigs as affected by dietary cation anion difference and nonstarch polysaccharide," J. Animal Sci. 79(7):1840-1848.

Dikeman et al., 2007, "Food Intake and Ingredient Profile Affect Viscosity of Ileal Digesta of Dogs," Animal Physiol. Animal Nutr. 91(3-4):130-138, Abstract.

Dobenecker et al., 2010, "High Calcium Intake Differentially Inhibits Nutrient and Energy Digestibility in Two Different Breeds of Growing Dogs," Animal Physiol. Animal Nutr. 94(5):109-114, Abstract.

Dzanis, 1997, "Selecting Nutritious Pet Foods," AAFCO US FDA Protecting and Promoting Your Health http://www.fda.gov/animalveterinary/resourcesforyou/ucm047120.htm, pp. 1-4.

Haydon et al., 1990, "Effect of dietary electrolyte balance on nutrient digestibility determined at the end of the small intestine and over the total digestive tract in growing pigs," J. Animal Sci. 68(11):3678-3693.

International Search Report and Written Opinion in International Application No. PCT/US06/061571, mailed Apr. 27, 2007.

International Search Report and Written Opinion in International Application No. PCT/US09/065499 mailed Apr. 6, 2010.

Klopfenstein et al., 2002, "Animal Diet Modification to Decrease the Potential for Nitrogen and Phosphorus Pollution," Council for Agricultural Science and Technology Issue Paper No. 21, pp. 1-16.

Mahan et al., 1999, "Effect of supplemental sodium chloride and hydrochloric acid added to initial starter diets containing spray-dried blood plasma and lactose on resulting performance and nitrogen digestibility of 3-week-old weaned pigs," J. Animal Sci. 77:3016-3021.

Moore et al., 2000, "Effects of Altering Dietary Cation-Anion Difference on Calcium and Energy Metabolism in Peripartum Cows," J. Dairy Sci. 83:2095-2104.

Pesti et al., 1999, "Studies on Semduramicin and Nutritional Responses: 3. Electrolyte Balance," Poultry Sci. 78:1552-1560.

Riond, 2001, "Animal Nutrition and Acid-Base Balance," Eur. J. Nutr. 40:245-254.

Roche et al., 2003, "Dietary Cation-Anion Difference and the Health and Production of Pasture-Fed Dairy Cows 1. Dairy Cows in Early Lactation," J. Dairy Sci. 86:970-978.

Roche et al., 2003, "Dietary Cation-Anion Difference and the Health and Production of Pasture-Fed Dairy Cows 2. Nonlactating Periparturient Cows," J. Dairy Sci. 86:979-987.

Uranaka, 1991, "Livestock Feed for Treating Diarrhoea etc.—Contains Living Microorganisms, Sodium Chloride, Potassium Chloride, Sodium Bicarbonate, Glucose and Clycine," Database WPI Thomson AN: 1991-121822, JP3061452 Abstract.

Weber et al., 2004, "Effect of Size on Electrolyte Apparent Absorption Rates and Fermentative Activity in Dogs," J. Animal Physiology and Animal Nutrition 88:356-365.

Willis, 2003, "The Use of Soybean meal and Full Fat Soybean Meal by the Animal Feed Industry," 12th Australian Soybean Conference http://www.australianoilseeds.com/_data/assets/file/0019/1198/Sarah_Willis-The_Use_of_Soybean_Mean_and_Full_Fat_Soybean_Meal_by_the_Animal_Feed_Industry.pdf, pp. 1-8.

COMPOSITIONS AND METHODS FOR ALTERING STOOL QUALITY IN AN ANIMAL

CROSS-REFERENCE TO RELATED APPLICATIONS

This application is a divisional of U.S. patent application Ser. No. 12/264,615 filed on Nov. 4, 2008, which is a divisional of U.S. patent application Ser. No. 11/774,975 filed Jul. 9, 2007, the contents of which are incorporated herein by reference in their entirety for all purposes.

The present invention relates generally to compositions and methods for improving stool quality and/or stool frequency for an animal by adjusting the balance of metabolizable cations to metabolizable anions consumed by the animal.

BACKGROUND OF THE INVENTION

Stool quality and stool frequency are generally determined by five factors: food ingredient digestibility, fiber level, health status, activity level, and water intake. When these factors are balanced, stools are generally formed, firm, dark, and exhibit a relatively reduced odor. Stools exhibiting these properties are considered to be good quality stools. If the factors are not balanced, stools are generally soft, loose, watery, light-colored, and exhibit a relatively increased odor. Stools exhibiting these properties, particularly loose, watery stools, are considered to be poor quality stools.

Poor stool quality and irregular stool frequency can be caused by various factors, e.g., abnormal intestinal motility, increases in intestinal permeability, the presence of nonabsorbable osmotically active substances in the intestine, or agents that cause diarrhea. Similarly, some animal foods, particularly those known in the art as chunk and gravy animal foods, can cause poor stool quality. Often, an animal consuming such foods has a fecal discharge that is irregular and undesirable. Such discharge is generally characterized by frequent loose, watery stools. In some instances, the discharge may be classified as diarrhea.

Accordingly, new methods and compositions are required which can affect stool quality of an animal. U.S. patent application Ser. No. 11/566,512 (the '512 application) filed Dec. 4, 2006 (the contents of which are herein incorporated by reference) discloses adjusting the balance of metabolizable cations to metabolizable anions consumed by the animal to affect stool quality. It has generally been found that increasing the balance of metabolizable cations to metabolizable anions will result in firmer stool quality and reduced stool output. Conversely, decreasing the balance of metabolizable cations to metabolizable anions will result in looser stool and increased stool output.

While the '512 application describes methods for altering stool quality and/or frequency for adult dogs, the dietary requirements of adult dogs and puppies are quite different. For example, puppies generally experience rapid growth and development; thus they generally require significantly more nutrition than adult dogs and of a different nutritional composition. For example, puppies require higher calcium levels due to their rapid bone growth. Similarly, the stool of adult dogs and puppies are typically of different quality and it is known that a dog produces substantially firmer stool than a puppy, partly in response to their different diets and nutritional requirements. Thus, the cation and anion balance disclosed in the prior art, while suitable for adult dogs, may be unsuitable for improving the stool quality of a puppy. The inventors of the present invention have discovered that the stool quality of a puppy may be improved by modifying the dietary cation and anion balance of a food composition consumed by the animal such that the dietary cation and anion balance is from about 50 to about 300 mEq.

SUMMARY OF THE INVENTION

It is one aspect of the present invention to provide compositions for improving stool quality for an animal; particularly for a growing dog. In one embodiment, the present invention is a food composition comprising metabolizable cations and metabolizable anions, said composition having a dietary cation to anion balance (DCAB) of from about 50 to about 300 mEq. The composition is ideally nutritionally complete for a puppy.

In additional embodiments, the composition may have a DCAB of from about 75 to about 250 mEq, from about 100 to about 150 mEq, or have a DCAB of about 125 mEq.

In some embodiments the compositions of the present invention may comprise cations chosen from calcium, sodium, potassium, magnesium, and mixtures thereof and may further comprise anions chosen from phosphorus, chloride, sulfur, and mixtures thereof.

In further embodiments, a composition of the present invention may comprise potassium citrate in the amount of from about 0.5% to about 1.0%, e.g., about 0.76%; and may further comprise sodium bicarbonate in an amount of from about 0.1% to about 0.5%, e.g., about 0.2%.

The compositions of the present invention may comprise soluble fiber in an amount of from about 1% to about 4%, e.g., about 3%. The soluble fiber may be chosen from beet pulp, guar gum, chicory root, psyllium, pectin, blueberry, cranberry, squash, apples, oats, beans, citrus, barley, peas, or mixtures thereof.

In additional embodiments, the compositions of the present invention may further comprise an omega-3 fatty acid in the amount of from about 0.1% to about 10%, e.g., about 0.18%. The omega-3 fatty acid may be chosen from DHA, EPA, ALA, octadecatetraenoic acid, and mixtures thereof.

The compositions disclosed herein may further comprise a gastrointestinal tract-improving agent, an anti-diarrhea agent, an anti-constipation agent, or a mixture thereof.

In further embodiments, the compositions of the present invention may be in the form of a dry, wet or semi-moist food or a treat, snack, supplement or partially or fully edible toy.

Additional aspects of the invention relate to methods for improving stool quality and/or stool frequency in a puppy. Thus, the present invention relates to a method for improving stool quality of a puppy comprising administering to the puppy a composition having a balance of metabolizable cations to metabolizable anions of from about 50 to about 300 mEq.

Another aspect of the invention relates to a method to improve stool quality of a puppy comprising increasing the dietary balance of metabolizable cations to metabolizable anions in the puppy. In particular embodiments, the balance of metabolizable cations to metabolizable anions may be increased by increasing the puppy's dietary intake of a metabolizable cation, by decreasing the puppy's dietary intake of a metabolizable anion or by both increasing the puppy's dietary intake of metabolizable cations and decreasing the puppy's dietary intake of metabolizable anions.

The invention also relates to a method for treating a puppy susceptible to or suffering from constipation, comprising adjusting the balance of metabolizable cations to metabolizable anions consumed by the puppy by an amount sufficient to improve stool quality by decreasing the balance of metabolizable cations to metabolizable anions consumed by the puppy to produce looser stool. In particular embodiments, the balance of metabolizable cations to metabolizable anions may be decreased by decreasing the amount of metabolizable cations consumed by the puppy, increasing the amount of metabolizable anions consumed by the puppy or by both decreasing the amount of metabolizable cations and increasing the amount of metabolizable anions consumed by the puppy.

The invention further relates to a method for treating a puppy susceptible to or suffering from diarrhea and/or loose stool, comprising adjusting the balance of metabolizable cations to metabolizable anions consumed by the puppy by an amount sufficient to improve stool quality by increasing the balance of metabolizable cations to metabolizable anions consumed by the puppy to produce firmer stool. In particular embodiments, the balance of metabolizable cations to metabolizable anions may be increased by increasing the amount of metabolizable cations consumed by the puppy, by decreasing the amount of metabolizable anions consumed by the puppy or by both increasing the amount of metabolizable cations and decreasing the amount of metabolizable anions consumed by the puppy.

In another aspect, the invention relates to a method for improving the stool quality of a puppy in need thereof comprising:
 a. adding a sufficient amount of metabolizable cations or metabolizable anions to a food composition to increase or decrease the DCAB of the food composition as desired;
 b. administering the food composition of step (a) to the puppy;
 c. evaluating the quality of stool produced by the puppy; and
 d. repeating steps (a)-(c) until the puppy produces a stool having desired qualities.

In another aspect, the invention relates to a method for treating a puppy susceptible to or suffering from constipation by modifying the stool quality of the puppy comprising:
 a. adding a sufficient amount of metabolizable anions to a food composition to decrease the DCAB of the food composition;
 b. administering the food composition of step (a) to the puppy;
 c. evaluating the quality of stool produced by the puppy; and
 d. repeating steps (a)-(c) until the puppy produces a stool having desired qualities.

In another embodiment, the invention relates to a method for treating a puppy susceptible to or suffering from diarrhea and/or loose stool by modifying the stool quality of the puppy comprising:
 a. adding a sufficient amount of metabolizable cations to the food composition to increase the DCAB of the food composition;
 b. administering the food composition of step (a) to the puppy;
 c. evaluating the quality of stool produced by the puppy; and
 d. repeating steps (a)-(c) until the puppy produces a stool having desired qualities.

With regard to any of the methods of the present invention, it is contemplated herein that said methods may comprise the administration of any of the compositions of the present invention, and may optionally further comprise the administration to the puppy of at least one compound chosen from one or more gastrointestinal tract-improving agents, and/or one or more anti-diarrhea agents and/or one or more anti-constipation agents. Furthermore, the metabolizable cations may include those chosen from calcium, sodium, potassium, magnesium, and mixtures thereof and pharmaceutically acceptable salts thereof. The metabolizable anions may include those chosen from phosphorus, chloride, sulfur, and mixtures thereof and pharmaceutically acceptable salts thereof.

In another embodiment the present invention relates to kits for altering stool quality of a puppy comprising any one or more of the following components:
 a nutritionally complete puppy food composition;
 metabolizable cations;
 metabolizable anions;
 a gastrointestinal tract-improving agent, an anti-diarrhea agent and/or an anti-constipation agent; and
 instructions for altering the stool quality of a puppy by increasing or decreasing the DCAB of the food composition using metabolizable anions and/or metabolizable cations to modify stool quality depending on the condition of stool of a puppy to be treated, optionally with or without the additional use of a gastrointestinal tract-improving agent, an anti-diarrhea agent and/or an anti-constipation agent.

In another embodiment, the present invention is directed to the use of metabolizable anions and metabolizable cations in the manufacture of a food composition to alter stool quality in a puppy in need thereof and wherein said food composition has a DCAB from about 50 to about 300 mEq.

DETAILED DESCRIPTION OF THE INVENTION

The present invention is specifically directed to improving puppy stool quality. It is contemplated herein, however, that the compositions and methods disclosed herein may be used with any animal, especially a growing animal, particularly a growing companion animal. The term "companion animal" refers to any animal that lives in close association with humans and includes, but is not limited to, canines and felines of any breed. For example, it is contemplated herein that this term may also encompass any animal whose diet may be controlled by humans and which may benefit from methods and feeding the compositions disclosed herein. These animals may include, for example, domesticated farm animals (e.g. cattle, horses, swine, etc.) as well as undomesticated animals held in captivity, e.g. in zoological parks and the like.

An animal is "susceptible to" a disease or condition if the animal exhibits symptoms that indicate that the animal is likely to develop the condition or disease. An animal is "suffering from" a disease or condition if the animal exhibits symptoms that are indicative that the animal has developed the condition or disease.

As used herein, the term "puppy" refers to an immature canine, typically between the ages of birth and 12 months.

As used herein, "altering stool quality", "modifying stool quality" or "improving stool quality" refers to modifying the stool of an animal to produce a desired firmness in the stool and/or a desired stool frequency. Generally, stools that are loose and watery are not desired, nor are stools that are so firm that constipation is observed. Thus, stool quality is improved in an animal experiencing diarrhea (e.g., frequent loose, watery stools) by causing the stool to be more firm and causing the animal to produce fewer stools; conversely, an animal experiencing constipation will benefit by a change in stool quality such that the stool is less firm. As described herein, such changes may be achieved by altering the animal's dietary cation-anion balance (DCAB). An increase in DCAB can cause stool to be firmer; a decrease in DCAB can cause stool to be less firm.

Stool quality may be scored according to methods familiar to one of skill in the art. For example, fecal quality is commonly assessed by those of skill in the art by visual scoring, e.g., ranking stool visually on a scale from grade 1-5 as follows:

Grade 1: Greater than two-thirds of the feces in a defecation are liquid. The feces have lost all form, appearing as a puddle or squirt.

Grade 2: Soft-liquid feces are an intermediate between soft and liquid feces. Approximately equal amounts of feces in a defecation are soft and liquid.

Grade 3: Greater than two-thirds of the feces in a defecation are soft. The feces retain enough form to pile but have lost their firm cylindrical appearance.

Grade 4: Firm-soft feces are an intermediate between the grades of firm and soft. Approximately equal amounts of feces in a defecation are firm and soft.

Grade 5: Greater than two-thirds of the feces in a defecation are firm. They have a cylindrical shape with little flattening.

See also, Sunvold et al., J Anim Sci 1995 73:1099-1109; U.S. Pat. No. 6,280,779; U.S. Pat. No. 5,616,569. Stool quality may also be assessed quantitatively using methods to determine the amount of moisture in the feces in g/kg (see, e.g., Yamka et al., 2006, Am J Vet Res, 67(1):88-94).

The balance of metabolizable cations to metabolizable anions in the present invention can be determined by any means known to skilled artisans. For example, one method for measuring the balance of metabolizable cations to metabolizable anions is to calculate the animal's dietary cation-anion balance (DCAB), which is determined by calculating the cumulative amount of cations regularly consumed by the animal and subtracting the cumulative amount of anions consumed by the animal. Cations may include, e.g., sodium, potassium, calcium, and magnesium cations, or any other ion having a positive charge, including amino acids. Anions may include, e.g., chloride, sulfur, and phosphorus anions, or any other ion having a negative charge, including amino acids. For example, the DCAB is determined by calculating the cumulative amounts of sodium, potassium, calcium, and magnesium cations regularly consumed by the animal and subtracting the cumulative amount of chloride, sulfur, and phosphorus anions regularly consumed by the animal. Thus, in one embodiment, the DCAB is determined in accordance with the following equation:

$$DCAB\ (mEq) = (Na+K+Ca+Mg) - (Cl+S+P)$$

For purposes of calculating the DCAB, sodium, potassium and chloride ions have a valance of 1, sulfur, calcium and magnesium ions have a valance of 2, and phosphorus ions have a valance of 1.8.

The inventors of the present invention have discovered that the stool quality of an animal, specifically, a growing dog, e.g., a puppy, can be improved by feeding the animal a composition having a DCAB of from about 50 to about 300 mEq.

As known in the art, a puppy's stool quality (i.e., an increase in stool firmness) may typically be increased by increasing the amount of soluble fiber in the diet. Similarly, a puppy's stool quality is typically decreased by decreasing the amount of soluble fiber in the diet. Soluble fibers are fibers which are resistant to digestion and absorption in the small intestine and undergo complete or partial fermentation in the large intestine, e.g., beet pulp, guar gum, chicory root, psyllium, pectin, blueberry, cranberry, squash, apples, oats, beans, citrus, barley, or peas. Significantly, the inventors of the present invention have found that the soluble fiber content of a food composition may be decreased while still maintaining the stool quality of a puppy by increasing the DCAB of the food composition.

In some embodiments, the balance of metabolizable cations to metabolizable anions consumed by the animal can be adjusted in conjunction with the administration of one or more anti-diarrhea agents (to treat or prevent diarrhea or overly loose stool) or anti-constipation agents (to treat or prevent constipation or overly firm stool). The term "anti-diarrhea agent" means any compound, composition, or drug useful for preventing or treating diarrhea, which are known by those of skill in the art. Examples of these agents include, but are not limited to, compounds such as atropine, diphenoxylate, loperamide, octreotide, and opium tinctures. The term "anti-constipation agent" means any compound, composition, or drug useful for preventing or treating constipation which are known by those of skill in the art. Such compounds include laxatives, e.g., psyllium, methylcellulose, docusate, mineral oil, milk of magnesia, and Epsom salts. Appropriate anti-diarrhea and anti-constipation agents, and amounts thereof for use with companion animals are familiar to one of skill in the art.

As contemplated herein, the compositions of the present invention are meant to encompass nutritionally complete and balanced pet food compositions (also referred to herein simply as "nutritionally complete pet food compositions"). Nutritionally complete pet food compositions, including nutritionally complete puppy foods, are familiar to one of skill in the art. For example, nutrients and ingredients such as those disclosed herein as well as others suitable for animal feed compositions, and recommended amounts thereof, may be found, for example, in the Official Publication of the Association of American Feed Control Officials ("AAFCO"), Inc., *Nutrient Requirements of Dogs and Cats,* 2006. For example, nutritionally complete foods may contain protein, fat, carbohydrate, dietary fiber, amino acids, minerals, vitamins, and other ingredients in amounts known by those of skill in the art.

Protein may be supplied by any of a variety of sources known by those skilled in the art, including plant sources, animal sources, or both. Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed.

Fat can be supplied by any of a variety of sources known by those skilled in the art, including meat, meat by-products, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources.

Carbohydrate may be supplied by any of a variety of sources known by those skilled in the art, including oat fiber, cellulose, peanut hulls, beet pulp, parboiled rice, corn starch, corn gluten meal, and any combination of those sources. Grains supplying carbohydrate include, but are not limited to, wheat, corn, barley, and rice. Carbohydrate content of foods may be determined by any number of methods known by those of skill in the art. Generally, carbohydrate percentage may be calculated as nitrogen free extract ("NFE"), which may be calculated as follows: NFE=100%−moisture %−protein %−fat %−ash %−crude fiber %.

Fatty acids for inclusion in the compositions of the present invention include omega 3 fatty acids such as docosahexanenoic acid (DHA), eicosapentaenoic acid (EPA), alpha-linolenic acid (ALA), octadecatetraenoic acid (stearidonic acid) or mixtures thereof.

Dietary fiber refers to components of a plant which are resistant to digestion by an animal's digestive enzymes. Dietary fiber includes soluble and insoluble fibers. Soluble fiber are resistant to digestion and absorption in the small intestine and undergo complete or partial fermentation in the large intestine, e.g., beet pulp, guar gum, chicory root, psyllium, pectin, blueberry, cranberry, squash, apples, oats, beans, citrus, barley, or peas. Insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber. Crude fiber includes indigestible components contained in cell walls and cell contents of plants such as grains, e.g., hulls of grains such as rice, corn, and beans.

Amino acids, including essential amino acids, may be added to the compositions of the present invention as free amino acids, or supplied by any number of sources, e.g., crude protein, to the compositions of the present invention. Essential amino acids are amino acids that cannot be synthesized de novo, or in sufficient quantities by an organism and thus must be supplied in the diet. Essential amino acids vary from species to species, depending upon the organism's metabolism. For example, it is generally understood that the essential amino acids for dogs and cats (and humans) are phenylalanine, leucine, methionine, lysine, isoleucine, valine, threonine, tryptophan, histidine and arginine. In addition, taurine, while technically not an amino acid but a derivative of cysteine, is an essential nutrient for cats.

The compositions of the present invention may also contain one or more minerals and/or trace elements, e.g., calcium, phosphorus, sodium, potassium, magnesium, manganese, copper, zinc, choline, or iron salts, in amounts required to avoid deficiency and maintain health. These amounts are known by those of skill in the art, for example, as provided in the Official Publication of the Association of American Feed Control Officials, Inc. ("AAFCO"), *Nutrient Requirements of Dogs and Cats,* 2006.

The compositions of the present invention may also include vitamins in amounts required to avoid deficiency and maintain health. These amounts, and methods of measurement are known by those skilled in the art. For example, the Official Publication of the Association of American Feed Control Officials, Inc. ("AAFCO"), *Nutrient Requirements of Dogs and Cats,* 2006 provides recommended amounts of such ingredients for dogs and cats. As contemplated herein, useful vitamins may include, but are not limited to, vitamin A, vitamin $B_1$, vitamin $B_2$, vitamin $B_6$, vitamin $B_{12}$, vitamin C, vitamin D, vitamin E, vitamin H (biotin), vitamin K, folic acid, inositol, niacin, and pantothenic acid.

The compositions of the present invention may additionally comprise additives, stabilizers, fillers, thickeners, flavorants, palatability enhancers and colorants in amounts and combinations familiar to one of skill in the art.

In one embodiment, the compositions of the present invention are provided as a food, e.g., a nutritionally complete pet food composition. In another embodiment, the compositions of the present invention may be in the form of a treat, snack, supplement, or partially or fully edible toy. Such items for consumption by a pet are known to those skilled in the art, and can include, for example, compositions that are given to an animal to eat during non-meal time, e.g., a dog biscuits, edible chew toys, etc.

Foods of any consistency or moisture content are contemplated, e.g., the compositions of the present invention may be, for example, a dry, moist or semi-moist animal food composition. "Semi-moist" refers to a food composition containing from about 25 to about 35% moisture. "Moist" food refers to a food composition that has a moisture content of about 60 to 90% or greater. "Dry" food refers to a food composition with about 3 to about 11% moisture content and is often manufactured in the form of small bits or kibbles. Also contemplated herein are compositions that may comprise components of various consistency as well as components that may include more than one consistency, for example, soft, chewy meat-like particles as well as kibble having an outer cereal component and an inner cream component as described in, e.g., U.S. Pat. No. 6,517,877. The kibble may then be dried and optionally coated with one or more topical coatings known by those skilled in the art, for example, flavors, fats, oils, powders, and the like.

In addition to the optional use of anti-diarrhea agents and anti-constipation agents in the methods of the present invention, in some embodiments, the balance of metabolizable cations to metabolizable anions consumed by the animal can be adjusted in conjunction with the administration of one or more compositions comprising a gastrointestinal tract-improving agent. "Gastrointestinal tract-improving agents" are generally probiotics and prebiotics.

Probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Probiotics may enhance an animal's systemic cellular immune responses and may be useful as a dietary supplement to boost natural immunity in otherwise healthy animals. Probiotics include many types of bacteria but generally are chosen from four genera of bacteria: *Lactobacillus acidophilus, Bifidobacteria, Lactococcus,* and *Pediococcus.*

Prebiotics are nondigestible food ingredients that beneficially affect host health by selectively stimulating the growth and/or activity of bacteria in the colon, and are known by those of skill in the art. For example, fructooligosaccharide (FOS) is found naturally in many foods such as wheat, onions, bananas, honey, garlic, and leeks. FOS can also be isolated from chicory root or synthesized enzymatically from sucrose. FOS fermentation in the colon results in a large number of physiologic effects including increasing the numbers of bifidobacteria in the colon, increasing calcium absorption, increasing fecal weight, shortening of gastrointestinal transit time, and possibly lowering blood lipid levels. The increase in bifidobacteria has been assumed to benefit health by producing compounds to inhibit potential pathogens, by reducing blood ammonia levels, and by producing vitamins and digestive enzymes. Probiotic bacteria such as *Lactobacilli* or *Bifidobacteria* are believed to positively affect the immune response by improving the intestinal microbial balance leading to enhanced antibody production and phagocytic activity of white blood cells.

The amount of probiotics and prebiotics to be administered to the animal is determined by the skilled artisan based upon the type and nature of the probiotic and prebiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, preferably from about 5 billion to about 10 billion live bacteria per day. Generally, prebiotics are administered in amounts sufficient to positively stimulate the healthy microflora in the gut and cause these "good" bacteria to reproduce. Typical amounts are from about one to about 10 grams per serving or from about 5 percent to about 40 percent of the recommended daily dietary fiber for an animal.

In another embodiment, the present invention provides kits suitable for improving stool quality and/or stool frequency for an animal. Said kits may comprise combinations of cations, anions, foods, other compounds, agents or medicaments, and instructions for using said kit components for improving stool quality and/or stool frequency for an animal in need thereof. For example, it is contemplated that kits of the present invention may comprise metabolizable cations chosen from calcium, sodium, potassium, magnesium, and mixtures thereof; metabolizable anions may be chosen from phosphorus, chloride, sulfur, and mixtures thereof. Any and all forms of said metabolizable cations and anions are contemplated, including pharmaceutically acceptable salt forms. The components of the kits may further comprise a gastrointestinal tract-improving agent, an anti-diarrhea agent and/or an anti-constipation agent and instructions for use thereof.

For example, a kit may comprise a nutritionally complete food, e.g., a puppy food in addition to a metabolizable cation, and/or a metabolizable anion with instructions regarding how to increase the DCAB of the food composition with the metabolizable cation and/or instructions as to how to decrease the DCAB of the food composition with metabolizable anions in order to achieve a desired improvement in stool quality in an animal in need thereof. In some embodiments, the kit may further comprise one or more anti-diarrhea agents, anti-constipation agents, and/or gastrointestinal tract-improving agents and instructions for use thereof with the food and metabolizable cations and anions. It is understood that addition of cations will cause the stool to be more firm; the addition of anions will cause the stool to be less firm. Based on the teachings of the present invention, one of skill in the art will understand how to modify the DCAB in the animal depending on the condition of the stool of the animal to be treated and the change in stool firmness desired.

The kit components may exist in a single package or separate packages as appropriate for the kit component. The term "single package" generally means that the components of a kit are physically associated in or with one or more containers and considered as a unit of manufacture, distribution, sale, or use. Containers include, but are not limited to, bags, boxes, bottles, shrink wrap packages, stapled or otherwise fixed components, or combinations thereof. A single package can be, for example, containers or individual food compositions physically associated such that they are considered a unit for manufacture, distribution, sale, or use.

In another embodiment, the present invention is directed to the use of metabolizable anions and metabolizable cations in the manufacture of a food composition to alter stool quality in an animal in need thereof, and wherein said food composition has a DCAB of from about 50 to about 300 mEq.

EXAMPLES

This invention can be further illustrated by the following examples, although it will be understood that the examples are included merely for purposes of illustration and are not intended to limit the scope of the invention unless otherwise specifically indicated.

Example 1

Ten weaned beagle puppies are used in stool studies to determine 1) if the DHA upgrade affects stool quality in puppies, 2) if stool quality can be improved through manipulation of dietary cation anion balance (DCAB) in puppies and 3) what effects decreasing levels of beet pulp in conjunction with DCAB manipulation have on puppy stool quality. The nutrient compositions of each food treatment are presented in Table 1. Each food is kibbled and formulated in accordance with AAFCO standards familiar to one of skill in the art (e.g., as may be found in AAFCO's nutrient guides for dogs and cats) and balanced to meet growing puppy requirements. Each food is fed for a period of one week and stool scores are recorded daily. Each stool sample is scored on a grading scale of 1 to 5 according to conventional methods as described hereinabove, wherein grade 1 reflects stool wherein greater than two-thirds of the feces are liquid, and grade 5 reflects stool wherein greater than two-thirds of the feces are firm.

TABLE 1

| Analyzed Nutrient Composition of Foods Fed to Dogs[a] | | | | | | | |
|---|---|---|---|---|---|---|---|
| Ingredient | Food_A | Food B | Food C | Food D | Food E | Food F | Food G |
| Crude Protein, % | 29.30 | 31.75 | 31.85 | 31.81 | 31.85 | 31.89 | 30.19 |
| Crude Fat, % | 19.62 | 19.95 | 20.01 | 19.96 | 20.01 | 20.02 | 20.41 |
| Calcium, % | 1.49 | 1.48 | 1.47 | 1.49 | 1.47 | 1.46 | 1.41 |
| Phosphorous, % | 1.23 | 1.20 | 1.21 | 1.20 | 1.21 | 1.22 | 1.22 |
| Sodium, % | 0.50 | 0.50 | 0.50 | 0.45 | 0.45 | 0.50 | 0.50 |
| Magnesium, % | 0.13 | 0.13 | 0.13 | 0.13 | 0.12 | 0.12 | 0.13 |
| Chloride, % | 1.09 | 1.09 | 1.09 | 0.55 | 0.55 | 0.56 | 0.72 |
| Sulfur, % | 0.37 | 0.40 | 0.39 | 0.40 | 0.39 | 0.39 | 0.37 |
| Potassium, % | 0.77 | 0.80 | 0.80 | 0.72 | 0.72 | 0.72 | 0.73 |
| Essential Fatty Acids, % | 4.24 | 4.78 | 4.82 | 4.78 | 4.82 | 4.80 | 4.67 |
| DHA, % | 0.02 | 0.18 | 0.18 | 0.18 | 0.18 | 0.18 | 0.18 |
| Beet Pulp | 5.50 | 5.50 | 3.00 | 5.50 | 3.00 | — | 5.50 |
| DCAB[b] | 8.5 | 16.5 | 3.7 | 126.2 | 113 | 102.3 | 87.3 |

TABLE 1-continued

Analyzed Nutrient Composition of Foods Fed to Dogs[a]

| Ingredient | Food_A | Food B | Food C | Food D | Food E | Food F | Food G |
|---|---|---|---|---|---|---|---|
| Average Age of dogs (years) | 0.256 | 0.276 | 0.292 | 0.312 | 0.332 | 0.352 | 0.386 |
| Stool Score[c] | 4.07 | 4.03 | 3.78 | 4.24 | 4.56 | 4.19 | 4.30 |
| Stool Count[d] | 58 | 35 | 46 | 71 | 82 | 89 | 67 |

[a] on Dry Matter Basis
[b] DCAB (mEq) = (Sodium + Potassium + Calcium + Magnesium) − (Chloride + Sulfur + Phosphorous)
[c] Stool scores were ranked from 1 to 5 according to conventional methods as described in text.
[d] Number of stools scored over seven-day period The results described in Table 1 indicate that increasing the DCAB of food compositions can cause the production of better quality (firmer) stool, even though amounts of soluble fiber are decreased. Specifically, the highest stool quality in puppies is achieved when beet pulp is lowered to 3.0% (from 5.5%) and DCAB is increased. Results also indicate that potassium chloride may be replaced by potassium citrate and sodium chloride may be replaced by sodium bicarbonate in the food compositions (data not shown).

Example 2

An additional study with the same 10 beagle puppies at an older age is repeated with Foods A, B, and E. Data for this study (including the average ages and weights of the dogs in the studies described in Example 1) are provided in Table 2. Data in the study using the older dogs confirm the results of Example 1.

TABLE 2

Stool Score, Stool Count, and Average Age and Weight for Puppies

| | Food A | Food B | Food C | Food D | Food E | Food F | Food G |
|---|---|---|---|---|---|---|---|
| EXAMPLE 1 | | | | | | | |
| Average Age, years | 0.256 | 0.276 | 0.292 | 0.312 | 0.332 | 0.352 | 0.386 |
| Average Body Weight, kg | 5.125 | 5.181 | 5.136 | 5.502 | 6.151* | 5.773 | 6.655 |
| Stool Score | 4.07 | 4.03 | 3.78 | 4.24 | 4.56 | 4.19 | 4.30 |
| Stool Count | 58 | 35 | 46 | 71 | 82 | 89 | 67 |
| EXAMPLE 2 | | | | | | | |
| Average Age, years | 0.406 | 0.426 | — | — | 0.446 | — | — |
| Average Body Weight, kg | 6.791 | 6.977 | — | — | 7.063 | — | — |
| Stool Score | 4.30 | 4.50 | — | — | 4.72 | — | — |
| Stool Count | 73 | 82 | — | — | 61 | — | — |

*One animal was not included in the average body weight calculation because of no available data.

In the specification, there have been disclosed typical embodiments of the invention and, although specific terms are employed, they are used in a generic and descriptive sense only and not for purposes of limitation. Obviously many modifications and variations of the invention are possible in light of the above teachings. It is therefore to be understood that the invention may be practiced otherwise than as specifically described.

As used herein and in the appended claims, the singular forms "a", "an", and "the" include plural reference unless the context clearly indicates otherwise. The terms "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of this invention. All patents, patent applications, publications, and other references cited or referred to herein are incorporated by reference in their entirety for all purposes.

What is claimed is:

1. A method for treating a puppy suffering from diarrhea and/or loose stool, comprising adjusting the balance of metabolizable cations to metabolizable anions in a food composition consumed by the puppy by an amount sufficient to improve stool quality of the puppy by increasing the balance of metabolizable cations to metabolizable anions consumed by the puppy to produce firmer stool, wherein the food composition has a dietary cation-anion balance (DCAB) of about 50 to about 300 mEq, and wherein the puppy consumes the food composition and the diarrhea and/or loose stool is treated.

2. The method of claim 1 wherein the balance of metabolizable cations to metabolizable anions is increased by increasing the amount of metabolizable cations consumed by the puppy to achieve the DCAB of about 50 to about 300.

3. The method of claim 1 wherein the balance of metabolizable cations to metabolizable anions is increased by decreasing the amount of metabolizable anions consumed by the puppy to achieve the DCAB of about 50 to about 300.

4. The method of claim 1 wherein the balance of metabolizable cations to metabolizable anions is increased by increasing the amount of metabolizable cations and decreasing the amount of metabolizable anions consumed by the puppy to achieve the DCAB of about 50 to about 300.

5. The method of claim 1 further comprising:
   a. evaluating the quality of stool produced by the puppy; and
   b. repeating the adjusting step and the evaluating step until the puppy produces firmer stool.

6. The method of claim 1, wherein the DCAB is about 100 to about 150 mEq.

7. The method of claim 1, wherein the DCAB is about 75 to about 250 mEq.

* * * * *